United States Patent
Pierce

4,087,450
May 2, 1978

[54] (POLYCHLOROPHENOXY) METHYL ESTERS OF THIOCYANIC ACID

[75] Inventor: James K. Pierce, Midland, Mich.

[73] Assignee: The Dow Chemical Company, Midland, Mich.

[21] Appl. No.: 762,970

[22] Filed: Jan. 27, 1977

Related U.S. Application Data

[63] Continuation of Ser. No. 366,897, Jun. 4, 1973, abandoned.

[51] Int. Cl.$^2$ .......................................... C07C 161/02
[52] U.S. Cl. .................................. 260/454; 424/302; 106/15 R; 71/67
[58] Field of Search ............................................ 260/454

[56] References Cited

U.S. PATENT DOCUMENTS

| 2,239,079 | 4/1941 | Coleman et al. | 260/454 |
| 3,632,771 | 1/1972 | Dolman et al. | 260/454 |

FOREIGN PATENT DOCUMENTS

| 165,814 | 11/1952 | Australia | 260/454 |
| 919,290 | 10/1954 | Germany | 260/454 |
| 7,909 | 3/1972 | Japan | 260/454 |

*Primary Examiner*—Lewis Gotts
*Assistant Examiner*—Robert C. Whittenbaugh
*Attorney, Agent, or Firm*—T. Post; D. L. DeJoseph

[57] ABSTRACT

(Polychlorophenoxy)methyl esters of thiocyanic acid of the formula

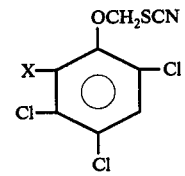

wherein X is hydrogen or chloro. The compounds are prepared by reacting substantially equimolar proportions of the appropriate polychloroanisole with phosphorous pentachloride at an elevated temperature to form the corresponding α,polychloroanisole and reacting the latter with potassium thiocyanate in an appropriate solvent at reflux temperature and recovering the (polychlorophenoxy)methyl ester of thiocyanic acid. The compounds have fungicidal and marine antifoulant activity.

3 Claims, No Drawings

(POLYCHLOROPHENOXY) METHYL ESTERS OF THIOCYANIC ACID

This is a continuation, of application Ser. No. 366,897 Filed June 4, 1973 now abandoned.

BACKGROUND OF THE INVENTION

Compounds of the formula

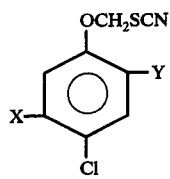

wherein X and Y both are hydrogen or wherein X is methyl and Y is hydrogen, or wherein X is hydrogen and Y is chloro are known; German Pat. No. 919,290. With reference to fungicidal activity against important fungi, they have a small fraction of the fungicidal activity of the compounds of this invention. The compound pentachloro-(thiocyanatomethoxy)- benzene is also known; Japanese Pat. application No. 7207910. Its fungicidal activity against important fungi is a small fraction of that of the compounds herein claimed.

SUMMARY OF THE INVENTION

This invention concerns compounds corresponding to the formula

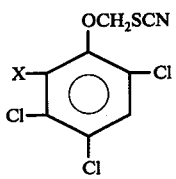

wherein X represents chloro or hydrogen. The compounds are colorless, acicular solids when recrystallized from hexane.

The compounds are prepared by reacting substantially equimolar proportions of polychloroanisole and phosphorous pentachloride with stirring and heating at an elevated temperature, advantageously between about 160° and about 200° C., until reaction is substantially completed as determined by the evolution of by-product phosphorous trichloride. The resulting α, polychloroanisole is dissolved in an appropriate solvent such as acetone, methanol or dimethyl sulfoxide and to the resulting solution is added dry potassium thiocyanate, advantageously in excess over an equimolar proportion, for example, between about 10 and 50% excess, and the mixture is stirred at a temperature between about 20° C. and reflux until the reaction is substantially completed as determined by formation of by-product potassium chloride.

Product (polychlorophenoxy)methyl ester of thiocyanic acid is recovered from the reaction medium by pouring the latter into ice water and extracting with ether, advantageously using multiple extractions. The ether extracts are washed with aqueous cold dilute alkali metal hydroxide or carbonate, advantageously sodium hydroxide or sodium carbonate, and with water, dried over magnesium sulfate and concentrated until product crystallizes out. The crude product is recrystallized from hexane to yield purified product as colorless needles.

DESCRIPTION OF THE PREFERRED EMBODIMENTS

The following examples further describe the invention and the manner and process of making and using it so as to enable the art skilled to make and use the invention, and set forth the best mode contemplated by the inventor of carrying out the invention.

EXAMPLE 1:

Preparation of Thiocyanic Acid, (2,4,5-Trichlorophenoxy)Methyl Ester (I)

In a 50 ml. flask equipped with a thermometer, magnetic stirrer, oil bath, and fractionating distillation head place 20.0 g. (0.095 mole) 2,4,5-trichloroanisole and 19.7 g. (0.095 mole) phosphorous pentachloride. The mixture is stirred and heated at 160° C. for 3 hours. As reaction takes place, phosphorous trichloride distills out of the flask. The mixture is heated at 180° C. for 0.5 hour, cooled, and the intermediate product α,2,4,5-tetrachloroanisole is distilled; b. p. 123° C. at 1.5 mm Hg., yield 18.6 g. (81%). This product is dissolved in 120 ml. acetone and 8.1 g. (0.083 mole) dried potassium thiocyanate is added in one portion. The mixture is stirred at ambient temperature for 48 hours, poured into 900 ml. ice water, and extracted with ether. The ether extracts are washed with cold 0.5 N sodium hydroxide and water, dried (MgSO$_4$), and concentrated. The crude product is recrystallized from hexane to give compound (I) 14.5g (71%), as colorless needles, m.p. 103°–105° C. Calcd. for C$_8$H$_4$Cl$_3$NOS: C, 35.78; H, 1.50; Cl, 39.61; N, 5.22; S, 11.94. Found: C, 35.71; H, 1.68; Cl, 39.2; N, 5.14; S, 11.99.

EXAMPLE 2:

Preparation of Thiocyanic Acid, (2,3,4,6-Tetrachlorophenoxy)Methyl Ester (II)

In a 250 ml. flask equipped with a thermometer, magnetic stirrer, oil bath, and fractionating distillation head place 74.35 g. (0.302 mole) 2,3,4,6-tetrachloroanisole and 62.97 g. (0.302 mole) phosphorous pentachloride. The mixture is stirred and heated at 180° C. for 3 hours and at 200° C. for 0.5 hour. The mixture is then cooled and the α,2,3,4,6-pentachloroanisole is distilled; b.p. 122°–124° C. at 1.0 mm. Hg, yield 45.6 g. (54%). This product is dissolved in 350 ml. methanol and 17.4 g. (0.179 mole) dried, powdered potassium thiocyanate is added in one portion. The mixture is stirred at reflux for 48 hours, poured into 3000 ml. ice water, and extracted with ether. The combined ether extracts are washed with 5% sodium carbonate and water, dried (MgSO$_4$), and concentrated. The crude product is recrystallized from hexane to give compound (II), 24.0 g. (48%), as colorless needles, m.p. 51°–53° C. Calcd. for C$_8$H$_3$Cl$_4$NOS: C, 31.71; H, 1.00; Cl, 46.80; N, 4,62; S, 10.58. Found: C, 32.14; H, 1.15; Cl, 48.81; N, 4.91.

The structures are confirmed by their ir and nmr spectra.

The compounds of the invention are useful as antimicrobials for the control of fungi and yeasts. This is not to suggest that all of the compounds are equally effective against all of the organisms at the same concentrations. For such uses, the compounds can be employed in an unmodified form or dispersed on a finely divided solid and employed as dusts. Such mixtures can also be dispersed in water with the aid of a surface-active agent and the resulting emulsions employed as sprays. In other procedures, the products can be employed as active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 1 to about 100 parts by weight of one or more of the compounds per million parts of such compositions.

Incorporation of the compounds of this invention into materials which are subject to fungal attack inhibits the growth of the fungi and preserves the original value of the materials. The compounds are sufficiently non-volatile and water insoluble that they will persist on or in such materials for long periods of time. Examples of materials which are adversely affected by fungal growth are latex and alkyd paint films, wood and wood products. The inventive compounds are sufficiently active against fungi that only small quantities are required to prevent mildew on paint films or wood-rot. The compounds are therefore useful for long-term protection against fungal growth in or on materials having a wood basis or a protective or decorative paint film subject to fungal attack.

In representative operations, the compounds of the present invention when tested for their activity as antimicrobials using conventional agar dilution tests give complete growth inhibition against *C. albicans, T. mentagrophytes, C. pelliculosa, R. nigricans, C. ips, C. fragans* and *Trichoderma sp.* 42. The following Table provides test data summaries in comparison with the activity of art compounds.

Table I

| Fungus | Concentration (ppm) for 100% Growth Inhibition | | | | | |
|---|---|---|---|---|---|---|
| | I | II | III* | IV* | V* | VI* |
| Candida albicans | 10 | 10 | 500 | 500 | 100 | >500 |
| Trichophyton mentagrophytes | 0.1 | 1 | 100 | 100 | 1 | 100 |
| Candida pelliculosa | 10 | 10 | 500 | 500 | 10 | >500 |
| Pullularia pullulans | 10 | 1 | 500 | 500 | 10 | >500 |
| Ceratocystis ips | 1 | 1 | 500 | 500 | 10 | >500 |
| Trichoderma species 42 | 10 | 1 | 100 | 100 | 10 | >500 |
| Rhizopus nigricans | 10 | 100 | 500 | 500 | 10 | >500 |

*Prior art compounds

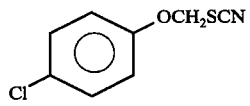

(III)

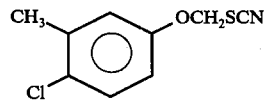

(IV)

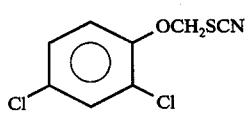

(V)

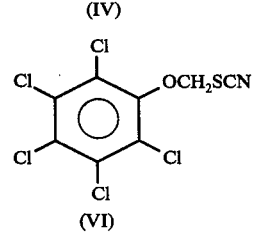

(VI)

With the exception of compound (VI), the compounds of this invention differ from the prior art compounds in the physical properties which are important for persistent fungicides, viz, low volatility and low water solubility. These differences are demonstrated below.

To determine volatility and water solubility of the compounds, the following procedure was used: A 0.1 g. portion of each compound was dissolved in 2.0 ml. acetone. One-half of this solution was placed on a dry, pre-weighed, 7 cm. diameter sheet of glass fiber paper (Reeve Angel #934AH). The fiber paper was allowed to air dry for 24 hours and was re-weighed to determine the amount (0.05 g.) of the compound present. The other half of the solution was used to impregnate similarly another sheet of glass fiber paper. For the volatility determination, one of the papers was placed in a 50° C. oven for 7 days, removed, air cooled for 24 hours, and weighed. The percent retention given in Table II was calculated by the following formula:

$$\% \text{ Retention} = \frac{(\text{Wt. of compd. remaining}) (100)}{(\text{Wt. of compd. deposited})}$$

For the water-leachability determination, the second impregnated paper was leached for 8 hours with 20° C. water running at 10 ml./sec. The fiber paper was allowed to air dry for 24 hours, then re-weighed. The percent retention was also calculated by the above formula. The figures recorded in following Table II represent the average of duplicate determinations.

Table II

| Compound | Percent Retention | |
|---|---|---|
| | Volatility | Water Extraction |
| I | 74 | 92 |
| II | 49 | 96 |
| III* | 2 | 80 |
| IV* | 12 | 71 |
| V* | 6 | 52 |
| VI* | 97 | 98 |

*Prior art compounds

Using a modification of ASTM D-1006, clear sapwood ponderosa pine boards ½ inch × 6 inches × 36 inches were primed with an unpreserved alkyd coating. A single coat of paint (alkyd or acrylic latex) incorporating compound (I) was brush applied. The boards were then exposed to the elements at Lake Jackson, Texas, and periodically readings were taken using the following rating scale:

| | | | |
|---|---|---|---|
| 1. | No mold growth | 6. | 50-70% growth |
| 2. | Trace, <5% growth | 7. | 70-90% growth |
| 3. | Trace, 5-10% growth | 8. | 90-95% growth |
| 4. | 10-25% growth | 9. | 100% growth |
| 5. | 25-50% growth | 10. | 100% growth, severe |

Results of this outdoor exposure test are summarized in following Tables III and IV.

Table III

| Wt. % (I) in Formulation | Preservation of Acrylic Latex Paint | | | |
|---|---|---|---|---|
| | 4 Mo. | 5 Mo. | 8 Mo. | 10 Mo. |
| 1.0 | 1 | 1 | 1 | 2 |
| 0.5 | 1 | 1 | 1 | 2 |
| 0.0 (control) | 10 | 10 | 10 | 10 |

Table IV

| Wt. % (I) in Formulation | Preservation of Alkyd Paint | | | |
| --- | --- | --- | --- | --- |
| | 4 Mo. | 5 Mo. | 8 Mo. | 10 Mo. |
| 1.0 | 1 | 1 | 1 | 2 |
| 0.8 | 4 | 3 | 1 | 2 |
| 0.6 | 8 | 9 | 1 | 2 |
| 0.4 | 9 | 9 | 1 | 2 |
| 0.0 (control) | 10 | 10 | 10 | 10 |

The compounds of this invention also repel or are toxic towards lower forms of marine life such as barnacles, and thereby function effectively as marine antifoulants. In evaluating marine antifoulant activity, a comparison of compound (I) vs. a standard antifouling toxicant, bis(tri-n-butyltin) oxide (TBTO), was carried out by treating pre-weighed 2½ inch by 2½ inch by ¼ inch porous silica test panels with a solution of the individual compound in methyl isobutyl ketone, allowing the solvent to air dry to constant weight, and then immersing the panels in seawater at a subtropical location which has dense populations of fouling organisms. Under these conditions, an untreated panel became completely fouled after two months' exposure. The anti-fouling activity of compound (I) in comparison with TBTO is demonstrated in following Table V.

Table V

| Organisms | Percent Fouling of Test Panels | |
| --- | --- | --- |
| | Compound I (0.14 g. in panel) | TBTO (0.13 g. in panel) |
| Barnacles | 0% | 0% |
| Encrusting Bryozoans | 0 | 0 |
| Algae | 0 | 0 |
| Algae Spores | 30 | 20 |
| Hydroids | 0 | 0 |
| Oysters | 0 | 0 |
| Tube Worms | 0 | 0 |
| Tunicates | 0 | 0 |
| Microfouling | 0 | 0 |

What is claimed is:

1. A compound corresponding to the formula

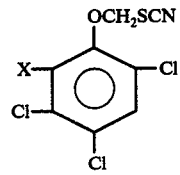

wherein X represents chloro or hydrogen.

2. The compound of claim 1 which is 2,4,5-trichlorophenoxymethyl thiocyanate.

3. The compound of claim 1 which is 2,3,4,6-tetrachlorophenoxymethyl thiocyanate.

* * * * *

UNITED STATES PATENT AND TRADEMARK OFFICE
CERTIFICATE OF CORRECTION

PATENT NO. : 4,087,450
DATED : May 2, 1978
INVENTOR(S) : James K. Pierce

It is certified that error appears in the above-identified patent and that said Letters Patent are hereby corrected as shown below:

Column 1, line 55 "about 10 and 50%" should read
-- about 10 and about 50% --;

Column 6, line 26 "which is 2,4,5-trichloro-"
should read -- which is methyl 2,4,5-trichloro --;

Column 6, line 28 "which is 2,3,4,6-tetra-" should read
-- which is methyl 2,3,4,6-tetra- --.

Signed and Sealed this

Nineteenth Day of September 1978

[SEAL]

Attest:

RUTH C. MASON
Attesting Officer

DONALD W. BANNER
Commissioner of Patents and Trademarks